(12) United States Patent
Johnson

(10) Patent No.: US 6,426,168 B1
(45) Date of Patent: Jul. 30, 2002

(54) METHOD OF INSPECTING PHOTO MASKS

(75) Inventor: Kurt A. Johnson, Underhill, VT (US)

(73) Assignee: International Business Machines Corporation, Armonk, NY (US)

(*) Notice: Subject to any disclaimer, the term of this patent is extended or adjusted under 35 U.S.C. 154(b) by 51 days.

(21) Appl. No.: 09/638,583

(22) Filed: Aug. 15, 2000

(51) Int. Cl.$^7$ .............................. G03C 5/00; G03F 9/00; G06K 9/00
(52) U.S. Cl. .................. 430/30; 430/394; 382/144; 382/145; 382/149
(58) Field of Search ................... 430/30, 394; 382/144, 382/145, 149

(56) References Cited

U.S. PATENT DOCUMENTS

| | | | |
|---|---|---|---|
| 4,718,767 A | 1/1988 | Hazama | 356/381 |
| 5,123,743 A | 6/1992 | Feldman | 356/394 |
| 5,811,223 A | 9/1998 | Bae | 430/312 |
| 5,828,457 A | 10/1998 | Tabata et al. | 356/394 |
| 5,976,738 A | 11/1999 | Nakashima | 430/22 |

Primary Examiner—Christopher G. Young
(74) Attorney, Agent, or Firm—Schmeiser, Olsen & Watts; William D. Sabo

(57) ABSTRACT

A method of inspecting photo masks by patterning at least one image in a first region of a substrate using a first photo mask, patterning at least one second image in a second region of the substrate using a second photo mask, wherein the first and second regions are substantially near one another. Comparing the first and second images to determine if the first photo mask forms a pattern substantially similar to the image formed by the second mask.

20 Claims, 3 Drawing Sheets

METHOD OF INSPECTING PHOTO MASKS

BACKGROUND OF THE INVENTION

1. Technical Field

The present invention relates generally to semiconductor manufacturing, and more particularly, to the inspection of semiconductor photo masks.

2. Related Art

In semiconductor manufacturing, photo masks used in the fabrication of semiconductor devices may be added and/or replaced throughout processing. The additional/replacement photo mask, however, must pattern images at the wafer level that are identical to the images formed by the previously used photo mask. For ease of comparison, the images are typically formed side by side on a single wafer using both the additional/replacement photo mask and the previously used photo mask.

Heretofore, the images were compared by applying a first photo resist to a first region of a wafer, exposing the first photo resist using a first mask within the first region, developing the first photo resist, etching a first image into an etchable layer of the first region, and stripping the excess photo resist. A second photo resist was then applied to a second region of the wafer, the second photo resist was exposed using a second mask within the second region, and the second photo resist was developed. Thereafter, the etched image in the first region was compared to the photo image in the second region. This process was time consuming due to the numerous processing steps and equipment required to form each image. Accordingly, there exists a need in the semiconductor industry for a method of quickly and effectively comparing photo masks.

SUMMARY OF THE INVENTION

A first general aspect of the present invention provides a method of comparing a first photo mask and a second photo mask, comprising: providing a substrate; applying a first resist on a surface of the substrate; removing a portion of the first resist from the surface of the substrate; applying a second resist on the surface of the substrate; patterning a first image within the first resist using the first photo mask; patterning a second image within the second resist using the second photo mask; and comparing the first image and the second image.

A second general aspect of the present invention provides a method of comparing a first photo mask and a second photo mask, comprising: providing a substrate; applying a first resist in at least one first region of the substrate; applying a second resist in at least one second region of the substrate; patterning a first image within the first resist using the first mask; patterning a second image within the second resist using the second mask; and comparing the first and second patterned images.

A third general aspect of the present invention provides a method of comparing patterned images comprising: providing a substrate; applying a first resist in a substantially circular pattern; applying a second resist in substantially circular ring pattern surrounding the first resist; patterning the first and second resists to form a first and a second patterned image; and comparing the first and second patterned images.

The foregoing and other features of the invention will be apparent from the following more particular description of the embodiments of the invention.

BRIEF DESCRIPTION OF THE DRAWINGS

Specific embodiments of this invention will be described in detail, with reference to the following figures, wherein like designations denote like elements, and wherein.

DESCRIPTION OF THE PREFERRED EMBODIMENTS

Although certain embodiments of the present invention will be shown and described in detail, it should be understood that various changes and modifications may be made without departing from the scope of the appended claims. The scope of the present invention will in no way be limited to the number of constituting components, the materials thereof, the shapes thereof, the relative arrangement thereof, etc. Although the drawings are intended to illustrate the present invention, the drawings are not necessarily drawn to scale.

Figure 1:
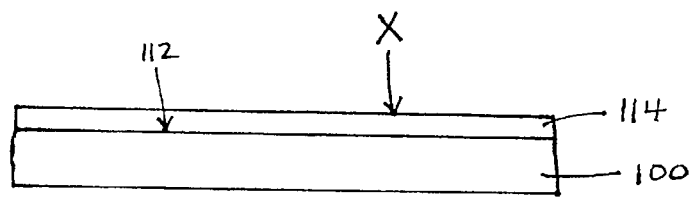
FIG. 1 depicts a cross-sectional view of a wafer having a first resist thereon.

FIG. 1 depicts a wafer 100 in accordance with a first embodiment of the present invention. The wafer 100 comprises silicon, or other similar semiconductor material(s). Within a resist apply module 210 of a photo processing unit 200 (see FIG. 7), a first surface 112 of the wafer 100 is coated with a first layer of photo resist 114 (hereinafter referred to as the "first resist"), using conventional spin-apply techniques. In particular, a first tip of a dispensing nozzle (not shown) within the resist apply module 210 dispenses the first resist 114 on the surface 112 of the wafer 100. The first resist 14 may comprise a mid-UV (ultra-violet) photoresist, either positive or negative, a deep-UV (DUV) photoresist, either positive or negative, or other similar material.

Figure 2:
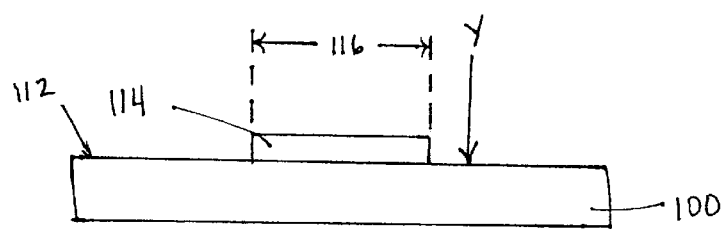
FIG. 2 depicts the wafer of FIG. 1 having a portion of the first resist removed.
Figure 3:
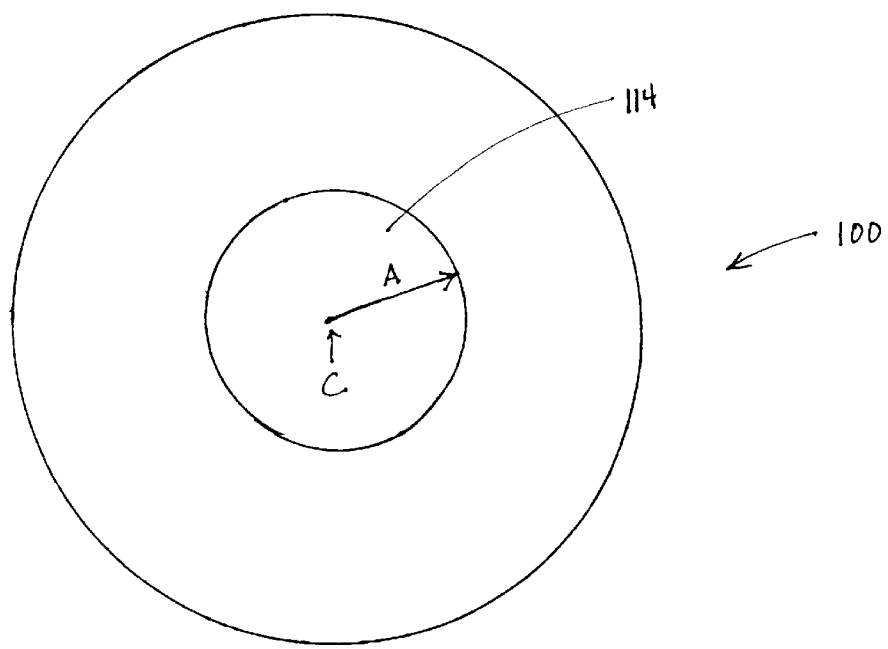
FIG. 3 depicts a top view of the wafer of FIG. 2.

Within the resist apply module 210 (FIG. 7), a second tip of the dispensing nozzle is moved, via an assembly arm, to a location X above the wafer 100, and begins dispensing a solvent onto the surface 112 of the wafer 100 to selectively remove portions of the first resist 114. As the wafer 100 is spinning, the solvent spreads from location X toward the edge of the wafer 100, thereby removing all the first resist 114 in that region of the wafer 100. Accordingly, the first resist 114 remains on the surface 112 of the wafer 100 in a first region 116, defined by a circle having a radius A from a center C of the wafer 100, as illustrated in FIGS. 2 and 3 (wherein FIG. 3 shows a top view of the wafer 100).

Figure 4:
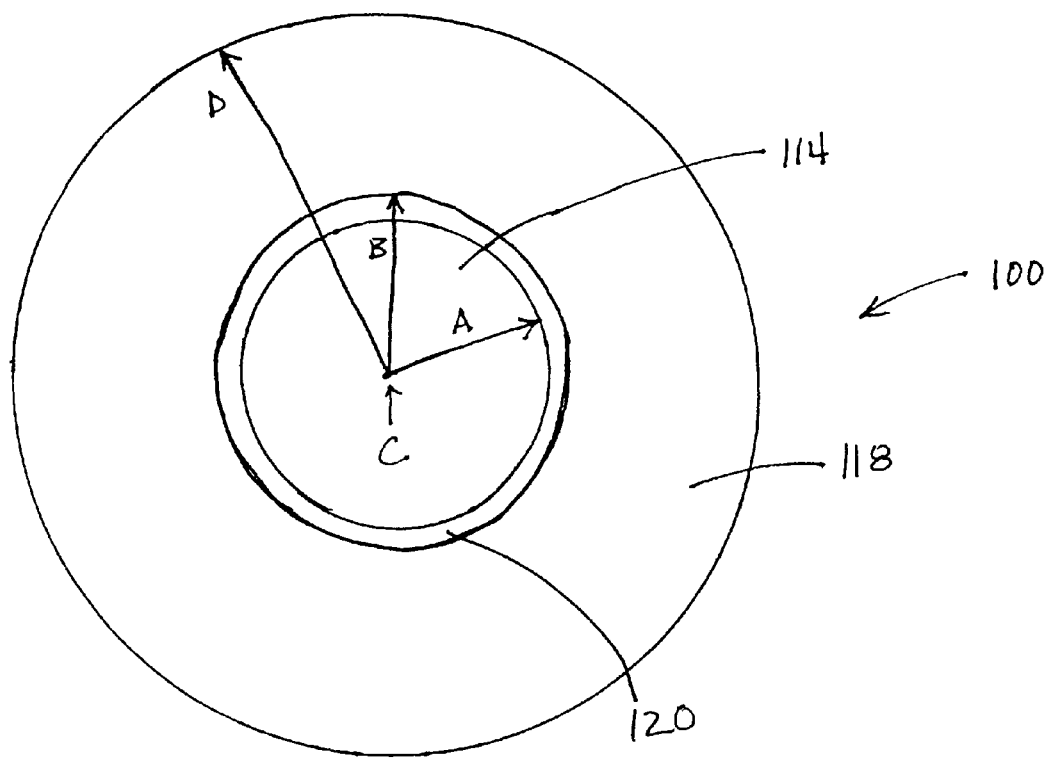
FIG. 4 depicts the wafer of FIG. 3 having a second resist applied to the surface.
Figure 5:
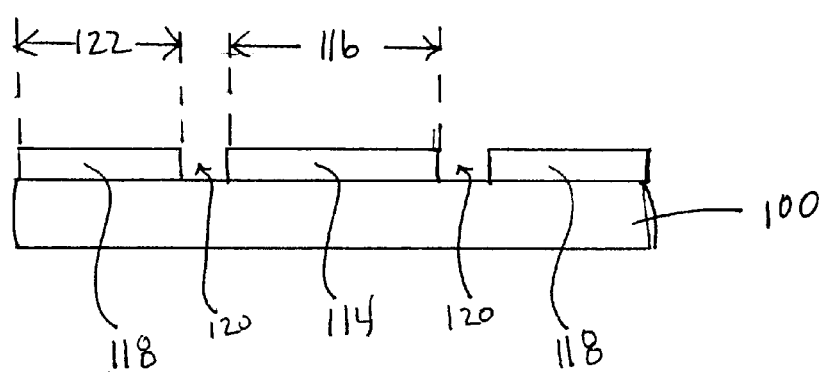
FIG. 5 depicts a cross-sectional view of the wafer of FIG. 4.

Within the resist apply module 210 (FIG. 7), the wafer 100 is coated with a second layer of photoresist 118 (hereinafter referred to as "second resist"), using conventional spin-apply techniques. In particular, the dispensing nozzle is moved to a location Y on the surface 112 of the wafer 100 (refer to FIG. 2), approximately 2–3 mm from the first region 116 (depending upon the accuracy of the dispensing assembly used). A third dispensing tip of the dispensing nozzle then dispenses the second resist 118 on the surface 112 of the wafer 100, thereby forming a second region 122, as shown in FIGS. 4 and 5. As with the first resist 114, the second resist 118 may comprise a mid-UV photoresist, either positive or negative, a DUV photoresist, either positive or negative, etc.

As illustrated in FIG. 4, the second region 122 forms a substantially circular ring around the first region 116, having a width of approximately radius D minus radius B. Likewise, a gap 120 is formed between the first and second regions 116, 122, such that the surface 112 of the wafer 100 is exposed, thereby separating the first and second resists 114, 118. The gap 120 has a width approximately equal to the radius B minus radius A, or approximately 2–3 mm in this 20 example. The gap 120 is formed because it is desirable to prevent the second resist 118 from overlapping the first resist 114.

After the wafer 100 has been coated with the first and second resists 114, 118, the wafer 100 is transported to a post apply bake module 214 (FIG. 7), wherein the wafer 100 is exposed to a temperature of approximately 80–120° C. for about 30–120 seconds.

Figure 6:
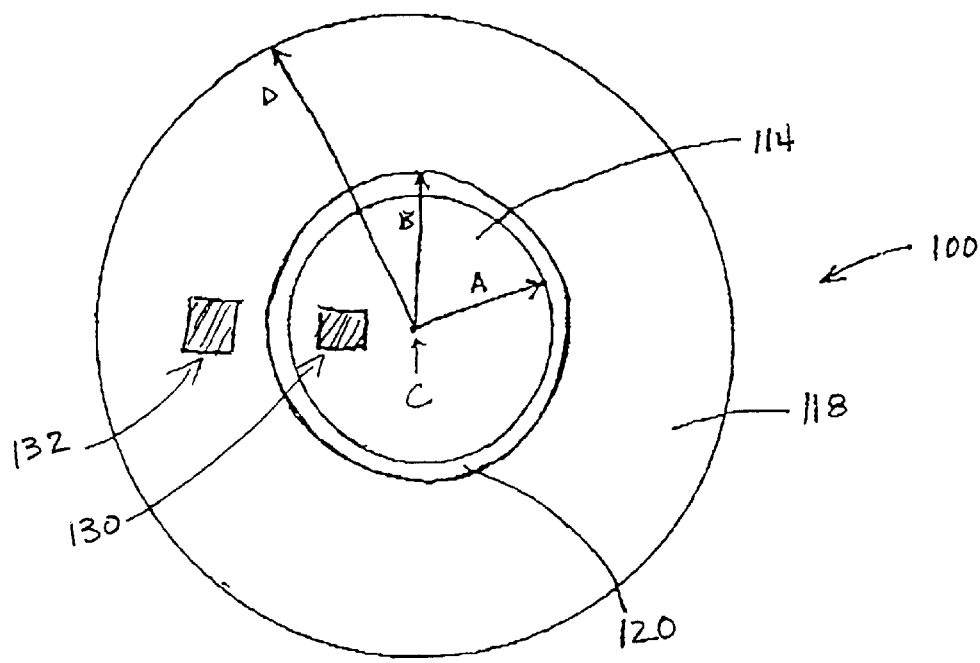
FIG. 6 depicts the wafer of FIG. 4 having a first and second image patterned within a first and second region, respectively.

The wafer 100 is then transported to an expose system 216 (FIG. 7), wherein a first image 130 is formed within the first region 116 of the wafer 100 using a first photo mask, hereinafter referred to as "Mask-1" (FIG. 6). In a similar manner, a second photo mask, hereinafter referred to as "Mask-2", is used to form a second image 132 within the second resist region 122 of the wafer 100.

Figure 7:
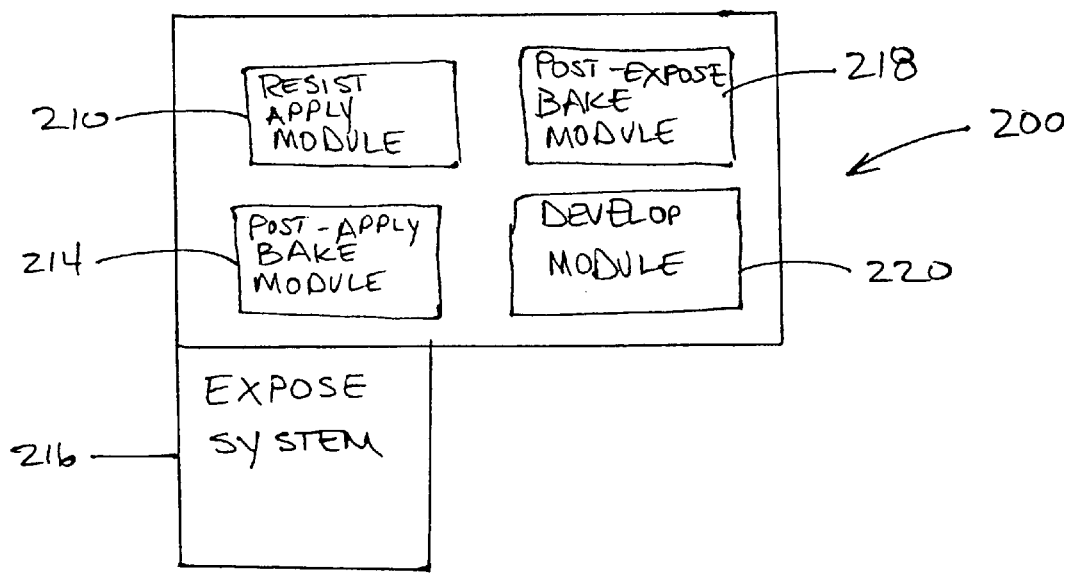
FIG. 7 depicts a plan view of a photo processing unit.

Following patterning of the first and second images 130, 132 within the first and second regions 116, 122 using Mask-1 and Mask-2, respectively, the wafer 100 is exposed to a post expose bake. In particular, the wafer 100 is exposed to a temperature in the range of approximately 80–120° C., for about 30–120 seconds within a post expose bake module 218 (FIG. 7).

The wafer 100 is then transported to a develop module 220 within the processing unit 200 (FIG. 7), where both the first and second resists 114, 118 within the first and second regions 116, 122, respectively, are developed to remove exposed material (in the event a positive photoresist is used), or to remove the un-exposed material (in the event a negative photoresist is used). Following the resist develop, the wafer 100 is removed from the photo processing unit 200, and transported to an inspection system. Therein the first image 130 formed within the first region 116 using Mask-1 is compared to the second image 132 formed within the second region 122 using Mask-2. For example, the two images 130, 132 patterned side-by-side on the wafer 100, are compared using an image comparison system or pattern comparison tool, such as a KLA 2135™ (made by KLA TenCor)

The existence of defects within the second region 122 indicates differences between Mask-1 and Mask-2, wherein Mask-1 is a production worthy control mask and Mask-2 is a new mask. "Defect" refers to a difference in the printed image formed by Mask-2 as compared with the printed image formed by Mask-1, such as a feature having a different size and/or shape, the absence of an image, the appearance of an additional image, etc. Therefore, the existence of defects within the second region 122 indicates that Mask-2 is defective, and cannot be used to replace Mask-1 in semiconductor production. If no defects are found in the second region 122 Mask-2 may be used to replace Mask-1 in semiconductor production.

It should be noted that the wafer 100 may be coated with the first and second resists 114, 118 within a single dispensing assembly 210, as described above. For instance, when the first resist 114 comprises a positive mid-UV resist, and the second resist 118 comprises a negative mid-UV resist, the first and second resists 114, 118 may be dispensed from a common nozzle assembly within the resist apply module 210. Likewise, positive and negative DUV resists, may be deposited within a common nozzle assembly within the resist apply module 210. However, in situations where one resist is a mid-UV and the other resist is a DUV, the first and second resists 114, 118 may need to be deposited within different resist apply modules.

It should likewise be noted that the first and second resists 114, 118 may be exposed within a single expose system 216. For instance, when the first resist 114 comprises a positive mid-UV resist, and the second resist 118 comprises a negative mid-UV resist, the first and second resists 114, 118 may be exposed within the same expose system 216. Likewise, positive and negative DUV resists, may be exposed within the same expose system 216. However, in situations where one resist is a mid-UV and the other resist is a DUV, the first and second resists 114, 118 must be exposed within different expose systems.

It should also be noted that the present invention is in no way intended to be limited to the use of just two resists, and/or two photo masks. The scope of the invention is intended to cover the use of more than two resists and corresponding regions on the surface 112 of the wafer 100. Each of the previous resist regions, starting with the second resist region 122, merely needs to be stripped within the resist apply module 210, as described above, and the wafer 100 may then be coated with additional layers of resist. Likewise, each additional region of resist may utilize a different photo mask, if so desired.

It should also be noted that the present invention provides a method of comparing images formed by at least two different masks, and/or different photoresist materials, without the need to remove the wafer 100 from the photo processing unit 200 (FIG. 7), unlike conventional methods. For example, the wafer 10 of the present invention does not need to be removed from the photo processing unit 200 to etch the first image, then returned to the photo processing unit 200 to pattern the second image, as is conventionally done. In fact, the present invention requires no etching.

It should be noted that because the layers of resist, having images patterned therein, are next to one another on the same wafer the comparison of the images, and therefore the masks that formed the images, is very quick and easy. Furthermore, all of the patterned images may be formed on the wafer 100 without leaving the photo processing unit 200, i.e., when comparing two different mid-UV resists, or two different DPV resists. However, it should be understood that in some instances it will be necessary to remove the wafer from the photo processing unit 200 to pattern the images, e.g., when comparing a mid-UV resist and a DPV resist.

It should be noted that the present invention is also contemplated for use in conjunction with masks having different magnifications. For instance, the present invention is useful when converting from a 1× mask to a 5× mask using either a positive or a negative mid-UV resist, or in the alternative, using two different resists either both positive or both negative.

It should also be noted that the first and second regions 116, 122 on the surface 112 of the wafer 100 are not limited in shape and/or size by the examples disclosed above. Furthermore, the regions are not limited to the placement on the wafer 100 illustrated above. For instance, the first region 116 may be formed on a left side of the wafer 100, while the second region 122 may be formed on a right side of the wafer 100, etc. So long as the regions 116, 122 are on the wafer 100 for ease of comparison, it is considered within the scope of the present invention.

While this invention has been described in conjunction with the specific embodiments outlined above, it is evident that many alternatives, modifications and variations will be apparent to those skilled in the art. Accordingly, the embodiments of the invention as set forth above are intended to be illustrative, not limiting. Various changes may be made without departing from the spirit and scope of the invention as defined in the following claims.

I claim:

1. A method of comparing a first photo mask and a second photo mask, comprising:

providing a substrate;

applying a first resist on a surface of the substrate;

removing a portion of the first resist from the surface of the substrate;

applying a second resist on the surface of the substrate;

exposing the first resist to pattern a first image within the first resist using the first photo mask;

exposing the second resist to pattern a second image within the second resist using the second photo mask;

then developing the first and second images; and comparing the first image and the second image.

2. The method of claim 1, wherein the first resist and the second resist comprise different materials.

3. The method of claim 1, wherein the first and second resists comprise a positive and a negative photo resist.

4. The method of claim 1, wherein the first and second photo masks pattern images having different magnifications.

5. The method of claim 1, wherein the second resist is applied at a location on the substrate spatially removed from the first resist.

6. The method of claim 1, further comprising:

baking the first and second resists following application of the second resist.

7. The method of claim 6, further comprising baking the first and second resists in a temperature of approximately 80–120° C. for about 30 seconds to 2 minutes.

8. The method of claim 1, further comprising:

baking the first resist following application of the second resist; and baking the second resists following application of the second resist.

9. The method of claim 8, further comprising baking the first and second resists in a temperature of approximately 80–120° C. for about 30 seconds to 2 minutes.

10. The method of claim 1, further comprising:

baking the first and second resists following patterning of the first and second resists.

11. The method of claim 10, further comprising baking the first and second resists in a temperature of approximately 80–120° C. for about 30 seconds to 2 minutes.

12. The method of claim 1, wherein the first and second photo masks are different masks.

13. The method of claim 1, wherein following comparing the first and second images, further comprises:

selecting the second photo mask if the second image formed by the second photo mask is substantially similar to the first image formed by the first photo mask.

14. The method of claim 1, wherein comparing the first and second images further comprises inspecting the first and second image using a pattern comparison tool.

15. A method of comparing a first photo mask and a second photo mask, comprising:

providing a substrate;

applying a first resist in at least one first region of the substrate;

applying a second resist in at least one second region of the substrate;

exposing the first resist to pattern a first image within the first resist using the first mask;

exposing the second resist to pattern a second image within the second resist using the second mask;

then developing the first and second images; and comparing the first and second patterned images.

16. The method of claim 15, wherein following applying the first resist further comprises: selectively removing the first resist from the at least one second region of the substrate before applying the second resist.

17. The method of claim 15, wherein comparing the first and second images further comprises inspecting the first and second image using a pattern comparison tool.

18. A method of comparing patterned images comprising:

providing a substrate;

applying a first resist on a surface of the substrate;

spinning the substrate;

applying a solvent to the surface of the spinning substrate to selectively remove a portion of the first resist;

applying a second resist adjacent the first resist;

patterning the first and second resists to form a first and a second patterned image; and comparing the first and second patterned images.

19. The method of claim 18, wherein patterning the first and second resists to form the first and second images further comprises:

exposing a first photo mask in a first region of the first resist and a second photo mask in a second region of the second resist; and developing the first and second resist.

20. The method of claim 18, wherein comparing the first and second patterned images further comprises inspecting the first and second image using a pattern comparison tool.

* * * * *